(12) United States Patent
Schrom et al.

(10) Patent No.: US 7,047,082 B1
(45) Date of Patent: May 16, 2006

(54) NEUROSTIMULATING LEAD

(75) Inventors: Mark G. Schrom, Hugo, MN (US); Paul J. Robinson, Mahtomedi, MN (US)

(73) Assignee: MicroNet Medical, Inc., White Bear Lake, MN (US)

( * ) Notice: Subject to any disclaimer, the term of this patent is extended or adjusted under 35 U.S.C. 154(b) by 0 days.

(21) Appl. No.: 09/500,213

(22) Filed: Feb. 8, 2000

Related U.S. Application Data

(63) Continuation-in-part of application No. 09/396,961, filed on Sep. 16, 1999, now abandoned.

(51) Int. Cl.
*A61N 1/05* (2006.01)

(52) U.S. Cl. ...................................... 607/116

(58) Field of Classification Search ........ 607/116–119, 607/122; 600/373, 374, 377, 379
See application file for complete search history.

(56) References Cited

U.S. PATENT DOCUMENTS

| | | | |
|---|---|---|---|
| 4,280,511 A | 7/1981 | O'Neil | |
| 4,355,646 A | 10/1982 | Kallok et al. | |
| 4,381,014 A | 4/1983 | Sandstrom et al. | |
| 4,432,377 A | 2/1984 | Dickhudt | |
| 4,437,474 A * | 3/1984 | Peers-Trevarton | 607/119 |
| 4,444,195 A * | 4/1984 | Gold | 607/122 |
| 4,559,951 A * | 12/1985 | Dahl et al. | 607/122 |
| 4,566,467 A | 1/1986 | DeHaan | |
| 4,590,950 A * | 5/1986 | Iwaszkiewicz et al. | 607/119 |
| 4,592,372 A | 6/1986 | Beranek | |
| 4,614,395 A | 9/1986 | Peers-Trevarton | |
| 4,706,682 A | 11/1987 | Stypulkowski et al. | |
| 4,764,324 A | 8/1988 | Burnham | |
| 4,848,352 A | 7/1989 | Pohndorf et al. | |
| 4,890,623 A | 1/1990 | Cook et al. | |
| 4,934,049 A | 6/1990 | Kiekhafer et al. | |
| 4,944,088 A | 7/1990 | Doan et al. | |
| 5,016,646 A * | 5/1991 | Gotthardt et al. | 607/122 |
| 5,040,544 A | 8/1991 | Lessar et al. | |
| 5,118,400 A | 6/1992 | Wollam | |
| 5,178,957 A | 1/1993 | Kolpe et al. | |
| 5,251,643 A * | 10/1993 | Osypka | 607/122 |
| 5,324,322 A | 6/1994 | Grill, Jr. et al. | |
| 5,374,285 A * | 12/1994 | Vaiani et al. | 607/117 |
| 5,417,208 A * | 5/1995 | Winkler | 607/122 |
| 5,431,681 A | 7/1995 | Helland | |
| 5,433,742 A * | 7/1995 | Willis | 607/122 |
| 5,458,629 A | 10/1995 | Baudino et al. | |
| 5,582,609 A | 12/1996 | Swanson et al. | |
| 5,609,622 A | 3/1997 | Soukup et al. | |
| 5,712,462 A | 1/1998 | Berkowitz et al. | |
| 5,762,631 A | 6/1998 | Klein | |
| 5,788,692 A | 8/1998 | Campbell et al. | |
| 5,796,044 A * | 8/1998 | Cobian et al. | 607/122 |
| RE35,924 E | 10/1998 | Winkler | |

(Continued)

*Primary Examiner*—George R. Evanisko
(74) *Attorney, Agent, or Firm*—Peter R. Lando

(57) ABSTRACT

A neurostimulating lead is provided for use in stimulating the spinal chord, spinal nerves, or peripheral nerves or for use in deep brain stimulation that comprises an elongated, flexible lead having improved steerability properties. The lead includes a plurality of thin-film metal electrodes connected by conductors embedded within the wall of the lead to electrical contacts at the proximal end of the lead. The lead is further designed to include an internal lumen for use with a guidewire in an over-the-wire lead placement.

29 Claims, 4 Drawing Sheets

U.S. PATENT DOCUMENTS

| | | | |
|---|---|---|---|
| 5,928,277 A | * 7/1999 | Laske et al. | 607/122 |
| 6,018,684 A | * 1/2000 | Bartig et al. | 607/122 |
| 6,151,520 A | 11/2000 | Combs | |
| 6,208,881 B1 | * 3/2001 | Champeau | 600/374 |
| 6,253,111 B1 | 6/2001 | Carner | |
| 6,324,415 B1 | 11/2001 | Spehr et al. | |

* cited by examiner

NEUROSTIMULATING LEAD

CROSS-REFERENCE TO RELATED APPLICATIONS

This application is a continuation-in-part of application Ser. No. 09/396,961, filed Sep. 16, 1999, now abandoned.

BACKGROUND OF THE INVENTION

1. Field of the Invention

This invention relates generally to implantable leads for conducting electrical signals to and/or from a stimulating pulse generator, and more particularly to neurostimulating leads having electrodes adapted for treatment of neurogenic, neuropathic or neuroceptive nerve conditions.

2. Discussion of the Related Art

Conventional neural stimulation therapies rely on electrode catheters for stimulating various regions of the spinal cord that correspond to each physiologic region of the body. Spinal cord stimulation, however, has limited effectiveness for certain pain conditions primarily due to limited accessibility to targeted nerves. In many cases where spinal cord stimulation is inadequate, spinal or peripheral nerves must be specifically stimulated to provide pain relief. However, with existing technology, nerve specific stimulation can only be accomplished with a surgical implant, which results in scarring and significant patient discomfort. Therefore, a need exists for a lead that provides greater specificity and increased accessibility to perform a broader array of nerve stimulation, while using less invasive methods to improve treatment outcome.

A variety of medical electrode catheters are available today for the diagnosis and treatment of various disorders of the cardiovascular and neurological systems. These electrode catheters can be used to sense electrical activity within the body and to deliver different forms of energy to stimulate, ablate, cauterize or pace. The core electrode technology common to all of these catheter designs is the application of one or more metallic bands on a catheter body. Examples of medical catheters using metallic banded electrodes include permanent and temporary cardiac pacing leads, electrophysiologic (EP) catheters, electrocautery probes and spinal stimulation catheters. The use of pre-formed metallic band electrodes manufactured from noble metals, such as gold or platinum and various other conductive alloys has found widespread application despite their functional design and performance limitations. Metallic band electrodes possess several distinct performance problems. When placed on flexible catheter materials, they add significant stiffness that greatly interferes with the steerability of such catheters. As such, prior art catheters having band electrodes are often restricted to applications where steerability and selective placement are not required. In addition, when DC or RF energy is applied to metallic band electrodes, a thermal field is generated which can interfere with energy delivery, increased power consumption and, in blood environments, create potentially life-threatening blood clots. Finally, the manufacture of catheters utilizing metallic band electrodes is quite labor intensive, resulting in high manufacturing costs.

Placement of leads for both external and implantable RF stimulating devices is quite simple for spinal cord stimulation. Here, a Tuohy needle is inserted into the spinal epidural space and the leads are placed adjacent to the targeted nerves addressing a specific painful region of the body. Relatively high power must be applied when directly stimulating the spinal nerves compared to that required when peripheral nerve stimulation is involved. While this is not a problem when the spinal leads are used with an external stimulator for which battery replacement is relatively easy. It is a major limitation of totally implantable systems in that high power consumption necessarily shortens the time between surgeries for battery replacement. Procedurally, nerve stimulation therapy becomes more challenging when spinal or peripheral nerves of the body are targeted. Due to the fact that many regions of the body cannot be effectively stimulated via the spinal cord, the only alternative in many cases is to surgically implant electrodes. Therefore, a significant need exists for therapeutic access to spinal and peripheral nerves without surgical intervention.

The neurostimulating leads of the present invention eliminate many of the problems encountered with conventional, band-electrode leads. The method employed in fabricating leads of the present invention afford the ability to fabricate highly flexible electrodes on extremely small diameter catheter lead bodies while, if desired, still providing a central lumen permitting such catheters to be advanced over a guidewire or with a stylet until the electrodes disposed thereon are positioned adjacent target tissue.

The present invention provides many improvements and advantages over the related art. The present invention to provides an improved method for fabricating electrical stimulating leads of reduced diameter and carrying a plurality of longitudinally spaced electrodes at the distal end thereof, each of the electrodes being individually connected to a connector at the proximal end thereof by conductors that are embedded within the wall of the lead body and insulated from one another. The present invention provides a method of fabricating such a lead while still maintaining a high degree of steerability thereof. The present invention provides an improved neurostimulating lead having a plurality of longitudinally-spaced, multi-layer, thin film electrodes proximate its distal end, where the electrodes are connected by spiral wound wires embedded in the wall of the lead body and where the lead body can, if desired, retain a central lumen through which a guidewire or stylet may pass. The present invention provides a construction of micro-lead catheters in very small diameters that maximizes inner lumen space for over-the-wire delivery, stylet insertion, infusion of fluids, multi-electrode lead wires and steering systems. The resulting leads provide enhanced sensitivity to low-level signals, providing improved output clarity and lower energy requirements when delivering stimulating currents to selected nerve tissue. Other improvements and advantages over the related art will be evident to those skilled in the art.

SUMMARY OF THE INVENTION

The foregoing improvements and advantages of the present invention are realized by devising a neurostimulating lead having an elongated, thin, flexible body member of a predetermined length and with annular wall defining an internal lumen that either extends from the proximal end to the distal end of that body member or over a sheet segment at the distal end of the body member. A plurality of spiral wound conductors are embedded within the wall of the body member and are electrically insulated from one another. They extend from the distal end to the proximal end of the body member. A plurality of multi-layer thin film metal electrodes are deposited on the outer surface of the annular wall of the body member at discrete longitudinally spaced locations in a zone proximate the distal end of the body member. To establish an electrical connection between the thin film electrodes and the buried spiral wound conductors, a plurality of tunnels are formed radially through the body member from the outer surface of the annular wall reaching the buried conductors. Laser etching is a preferred way of forming such tunnels. An electroplating operation or the application of a conductive epoxy is employed to create conductive links that extend through the tunnels from the buried conductors to the wall surface on which the thin film electrodes are later deposited. The lead further includes at least one connector at its proximal end. The connector includes a plurality of contacts that are electrically joined to the plurality of conductors. The connector is adapted to connect the lead to either an implanted or an external neurostimulator.

Utilizing the manufacturing method described herein, it has been possible to produce neurostimulating leads having an outer diameter of only 0.026 inch (about 2 French) and with an internal lumen diameter of about 0.012 inch, allowing the catheter to be passed over a 0.010 inch guidewire or stylet. The thin film electrodes are typically less than about 250 microns in thickness and, as such, do not detract from the flexibility of the resulting catheter and its ability to be readily steered through the epidural space and out through a selected intervertebral foramen beyond the dorsal or ventral root fibers and into the sheath surrounding the target peripheral nerves to be stimulated by using a guidewire or stylet delivery.

BRIEF DESCRIPTION OF THE DRAWINGS

The foregoing features, objects and advantages of the present invention will become apparent to those skilled in the art from the following detailed description of a preferred embodiment, especially when considered in conjunction with the accompanying drawings in which like numerals in the several views refer to corresponding parts.

DETAILED DESCRIPTION OF THE INVENTION

The present invention is provides a lead of the type typically used for neurostimulation. The invention is described in the context of a neurostimulating lead as a specific example for illustrative purposes only. The appended claims are not intended to be limited to any specific example or embodiment described in this patent. It will be understood by those skilled in the art that the lead of the present invention may be used for a wide variety of applications with only insubstantial changes to the apparatus and specifications as described below. These applications include, but are not limited to, spinal stimulation, peripheral nerve stimulation, deep brain stimulation, neuromonitoring, cardiac monitoring, cardiac rhythm management, ablation, mapping, or other medical applications using leads.

Figure 1:
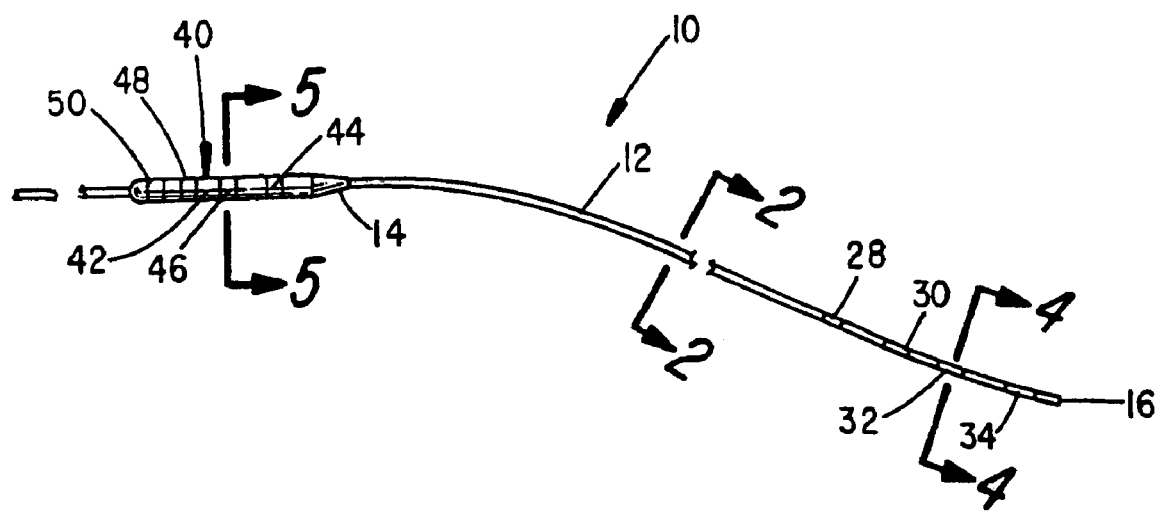
FIG. 1 is a partial perspective view of a neurostimulating lead constructed in accordance with the present invention.

Referring to FIG. 1, there is indicated generally by numeral 10 a neurostimulating lead constructed in accordance with the present invention. It is illustrated to include an elongated, flexible, plastic body member 12 having a proximal end 14 and a distal end 16 and a lumen 18 (FIG. 2) extending therebetween. The body member 12 is typically formed from a suitable medical grade polymer with polyurethane being preferred. The outside diameter of the body member 12 may be in a range of about 0.010 to 0.065 inch with 0.026 inch (2 French) being preferred. The inside diameter of the body member, i.e., the lumen 18 may be about 0.012 inch when the outside diameter is 2 French.

Figure 2:
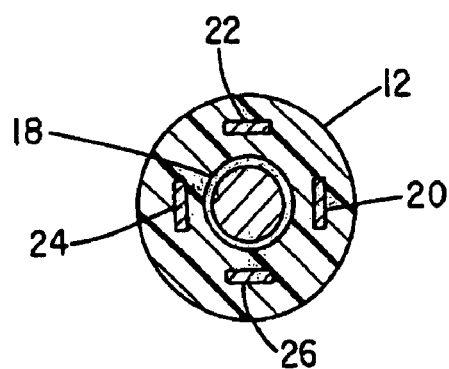
FIG. 2 is an enlarged cross-sectional view taken along the line 2—2 in FIG. 1.
Figure 3:
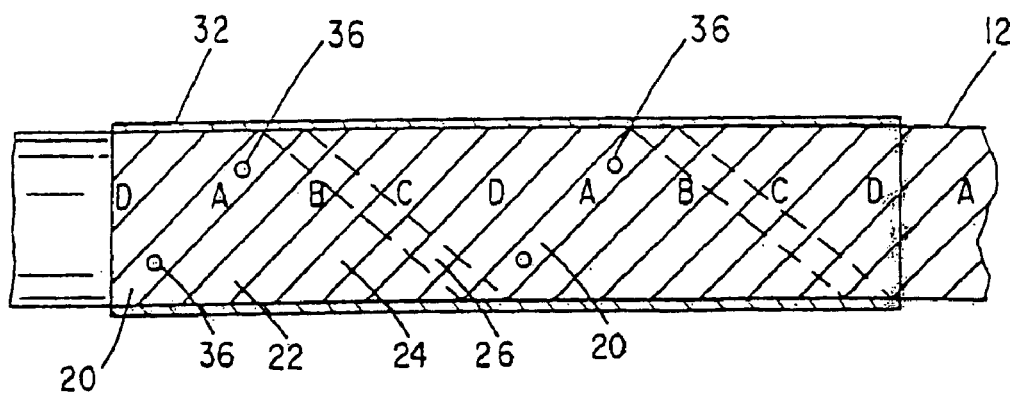
FIG. 3 is a greatly enlarged schematic illustration of a portion of the lead of FIG. 1 showing a thin film ring electrode deposited on the catheter as being transparent to show underlaying spiral wound conductors and the location of connecting links.

Referring again to the cross-sectional view of FIG. 2, it can be seen that there is embedded within the wall of the body member 12 a plurality of electrical conductors 20, 22, 24 and 26 which have a rectangular cross-section measuring approximately 0.004 inch in width and 0.002 inch in thickness. Other sizes and other cross-sectional shapes, such as oval, circular or square, may also be used for the conductors and, alternatively, a stranded conductor may be used. The enlarged schematic drawing of FIG. 3 shows that these relatively flat conductors are spiral wound and they extend from the proximal end 14 to the distal end 16 of the tubular catheter body 12. The spiral winding is such that each of the conductors is physically spaced from an adjacent neighbor and in that they are buried or submerged within the polymer comprising the body member 12, they are electrically insulated from one another. The pitch of the spiral windings may be such that the turns are at an angle of between about 10 to about 80 degrees to the longitudinal axis of the body member, it being understood that the pitch is directly dependent on the number of electrodes and therefore the number of conductors traversing the wall of the body member.

A plurality of longitudinally spaced electrodes 28, 30, 32 and 34 are deposited on a distal end portion of the catheter. These electrodes are formed using the method described in application of Eugene Champeau, Ser. No. 09/176,009, filed Oct. 20, 1998, now U.S. Pat. No. 6,208,881 entitled "Catheter With Thin Film Electrodes and Method for Making Same", which is assigned to the assignee of the present invention. The teachings of the Champeau application are hereby incorporated by reference. Each of the electrodes thus preferably comprises a plurality of superposed metallic layers, each exhibiting a nanocrystaline plate-like structure. As is explained in the Champeau application cited, the innermost metal film layer may typically be 5 microns or less in thickness and may be titanium, chromium, nickel or aluminum. By using a known ion-bombardment technique, the metal comprising the base layer is made to aggressively adhere to the outer surface of the polyurethane lead body 12. Next, a layer of metal, such as platinum or palladium may be deposited onto the base layer to a thickness in a range between, for example, 500 angstroms and 50 microns to serve as an oxygen diffusion barrier layer. Following that, a second intermediate conduction layer of gold, platinum, silver or copper may be deposited onto the exterior of the preceding layer in an ion-bombardment process and built up to a thickness in a range between a minimum of about 500 angstroms and a maximum of 250 microns or more. The outermost layer is selected for its bio-compatibility properties and high conductivity with gold, platinum or platinum iridium being preferred. The thickness of the outer layer may range from between about 500 angstroms and 50 microns. Each of the deposited electrodes 28, 30, 32 and 34 may be, for example, about 3 millimeter in length and may be, for example, separated from its adjacent electrode by a gap distance of about 4 millimeter, although the size and spacing of electrodes will vary depending on the particular application. Therefore, the examples for size and spacing are not intended to limit the scope of the present invention.

To establish an electrical connection between the embedded spiral-wound conductors and the individual thin film electrodes, before the thin film electrodes are deposited or otherwise formed on the surface of the body member, a laser beam is used to burn through the elastomeric wall of the body member to form tunnels to the conductors. The tunnels may be radially or otherwise oriented so as to allow the electrode to be conductively linked to the embedded conductor. Alternatively, the tunnels may be in the form an elongated channel or channels cut into the elongated body member substantially along a tangent to the body member. The elongated channel has a depth sufficient to extend through the elastomeric to allow a conductive link between the electrode and the embedded conductor. Once the tunnels are formed, an electroplating process or a conductive epoxy is used to create a conductive link through the tunnel extending from the embedded conductor to the exterior surface of the body member. When the thin film electrodes are deposited onto the wall surface, the conductive links provide an electrical connection between the electrodes and their respective individual conductors.

FIG. 3 schematically illustrates this arrangement. Here, four conductors labeled A through D are embedded within the wall of the body member 12 and a plurality of tunnels are represented on the drawing by the small circles 36. These tunnels penetrate through the wall 12 to contact only conductor A. Once the tunnels are formed, the lead may be placed in an electroplating bath with a DC voltage being applied to the conductor A at its proximal end. The plating bath will preferably contain free ions of a metal selected from the group including gold, silver, platinum, titanium, and platinum iridium. The application of the DC voltage will cause the metal ions to migrate through the tunnels, building up a conductive link therein in the same fashion that plated-through-holes on printed circuit boards are commonly fabricated. Alternatively, the conductive link may be achieved using a conductive epoxy. The conductive epoxy being directed through the tunnels to form an electrical connection between the embedded conductor and the electrode.

Figure 4:
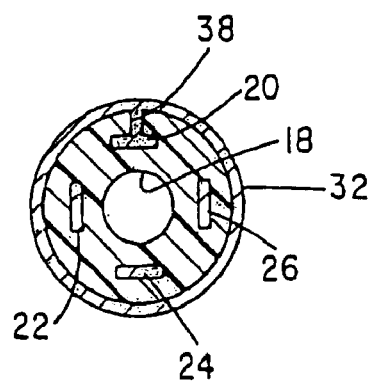
FIG. 4 is a cross-sectional view taken along the line 4—4 in FIG. 1.

Once the tunnels 36 have been filled, a thin film electrode, as at 28, may be deposited through a suitable mask onto the wall surface of the body member 12. The dimensions of the thin film electrodes may be established such that two connections are made with a given conductor. In FIG. 3, the thin film electrode 28 is shown with two connections to conductor A. This allows that a sufficient number of conductive links in the form of tunnels 36 to be made to join the electrode to its associated embedded conductor to insure a low ohmic coupling between the two. However, it is also possible to use a shorter electrode with a single connection to the conductor. In FIG. 3, the portion of the conductor A, traversing the far side of the catheter is shown in dashed lines. In the view of the FIG. 4, the conductive links joining the conductors 20–26 to the thin film electrodes 32 are identified by numeral 38.

Figure 6:
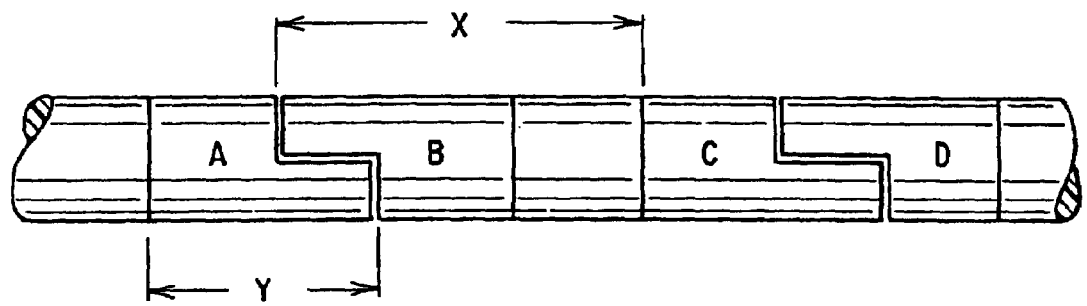
FIG. 6 is a segmented view of a distal end portion of a lead constructed in accordance with the present invention having longitudinally overlapping electrode segments.
Figure 7:
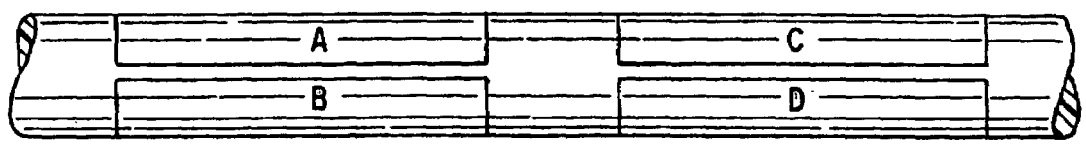
FIG. 7 is a segmented view showing a distal end portion of a lead with a different longitudinally overlapping electrode segment arrangement.

FIGS. 6 and 7, respectively show a preferred electrode arrangement wherein plural, longitudinally-spaced electrode structures, each comprising a bipolar pair of longitudinally overlapping conductive electrodes, where one is adapted to be connected to a positive voltage, the other to a negative voltage and either can be turned on or off by a physician at the time of lead implant. In FIG. 6, there are shown two pairs of electrodes, the first pair labeled A and B and the second pair C and D. Of course, more than two such pairs can be provided proximate the distal end portion of the lead. Each electrode segment, A, B, C, D, can be selectively connected to a positive or a negative polarity voltage or can be off, i.e., connected to neither. Each segment has a separate conductor connected to it leading back to a connector at the proximal end of the lead. In FIG. 6, the lead is masked such that when the thin film electrodes are deposited thereon, the segments A and B overlap one another over one-half their length. In the arrangement of FIG. 7, each electrode segment encircles the lead body over an arc slightly less than 180 degrees such that each electrode remains separate.

Using these arrangements, A may be designated to be positive when turned on and B may be negative when turned on. Likewise, C could be designated to be negative when turned on and D positive when turned on. If A and B are both turned on, the stimulating current would flow through nerve tissue bridging segments A and B. However, if A and C are both turned on with B and D both off, the stimulating current path is significantly longer, going from electrode segment A to electrode segment C.

To mate the lead 10 with a stimulating pulse generator, an in-line connector 40 is formed on the proximal end 14 of the lead body 12. The inline connector comprises a relatively inflexible, molded body 42 that is concentrically disposed over a portion of the lead 12 at its proximal end that supports a plurality of conductive contact rings 44–50 that are longitudinally spaced from one another along the length of the body member 42. The conductive rings are electrically connected to the embedded conductors 20–26 in a fashion substantially similar to that used in connecting the conductors to the ring electrodes 28–34. That is, tunnels are formed through the lead body 12 and an electroplating process or conductive epoxy is used to create conductive links leading to the deposited or sputtered metallization on the exterior surface of the lead body. Now, the preformed rings 44–50 of a substantial radial thickness can be slipped onto the proximal end of the lead body and into electrical contact with the metallized patterns on the lead body surface. Now, a suitable elastomer, such as silicone rubber or polyurethane, is injection molded over the rings to hold them in place. Any plastic material on the outer surfaces of the rings is removed to allow good ohmic contact with electrical contacts of the pulse generator. Alternatively, the inline connector is formed by the proximal end 14 of the lead body 12. The inline connector having a diameter substantially the same as the lead body 12 to allow a spinal access needle to pass over the in-line connector during implantation. This uniform diameter proximal end typically includes an adapter configured to electrically connect the lead to the stimulating pulse generator, as described above.

The connector body 42 also preferably has a central lumen allowing a guidewire or stylet to pass therethrough and through the lumen of the lead body 12 for over-the-wire placement of the lead. This same lumen can be used for fluid injection, drug delivery or other purposes known in the art. It is not essential to the invention that the lead body be tubular since a steerable tip may be provided on the distal end of the lead, obviating the need for a guidewire or stylet.

Figure 8:
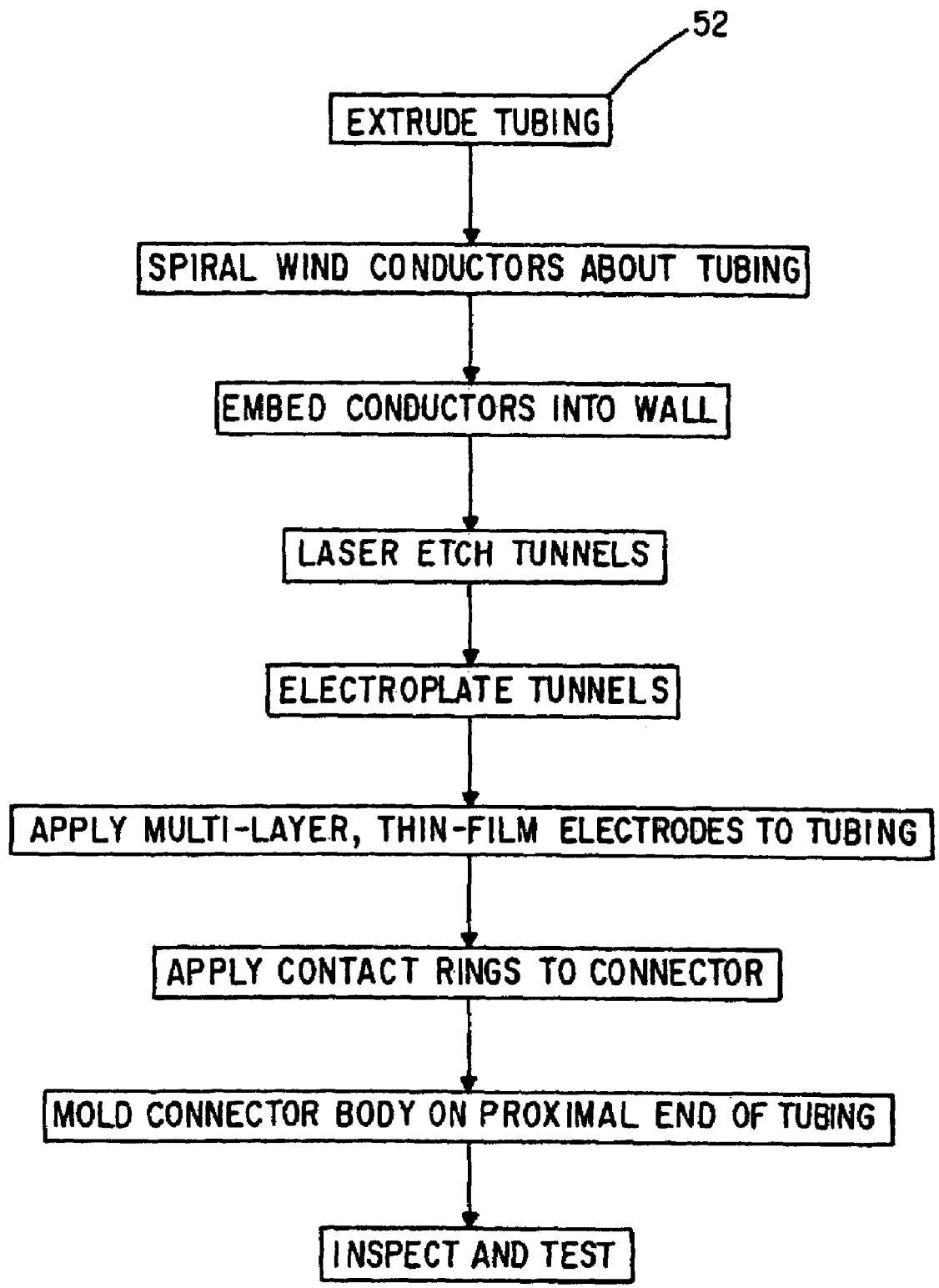
FIG. 8 is a process flow chart illustrating the steps involved in fabricating the neurostimulating lead of FIG. 1.

Having described the constructional features of the neurostimulating lead of the (present invention, consideration will next be given to the method or process for fabricating same, In this regard, reference is made to the block diagram process flow chart of FIG. 8.

The first step in the process, reflected by box 52 is to use a conventional extruder to form the body member from a suitable elastomeric material, preferably polyurethane. Typically, the body member is extruded over a mandrel. Knowing the number of electrodes and, therefore, the number of conductors needed to convey signals from and to those electrodes, a formula is applied to determine the O.D. of the tubing to be extruded so that when the conductors are embedded therein, the resulting subassembly will be of a specified O.D. desired, such as about 2 French The next step in the process is to spiral-wind and embed the conductors into the tubing wall and this is preferably accomplished using the method described and claimed in the U.S. Pat. No. 4,764,324 issued to Burnham, the teachings of which are hereby incorporated by reference. In accordance with the Burnham Patent, the extruded body member is heated to the point where, when the plurality of conductors are spirally wound under appropriate tension forces, the conductors will be submerged within the tubing wall. Subsequently, the outer surface of the catheter body member is smoothed by passing it through a heated dye to effectively remove any deformations created when the conductors are embedded within the catheter wall.

Figure 5:
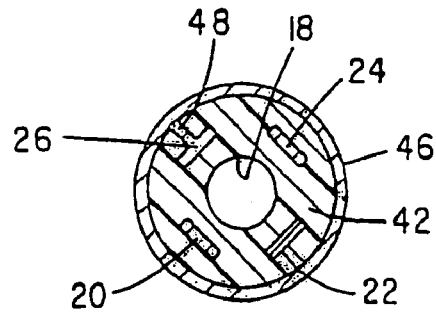
FIG. 5 is a cross-sectional view taken along the line 5—5 in FIG. 1.

Once the body member with the embedded conductors is completed as a subassembly, the mandrel will be removed and the catheter cut to a desired length. Next, the distal end portion of the lead body and a portion that is to become part of the connector at the proximal end are subjected to a laser etching process whereby tunnels are created that penetrate through the plastic down to the embedded conductors. Following that, the lead is placed in an electroplating bath or conductive epoxy is applied to create the conductive links, as at 38 and 48 in FIGS. 4 and 5, between the embedded conductor and the surface of the lead body and connector body.

Using the method set out in the aforereferenced Champeau patent application, multiple electrodes are vacuum-deposited onto the proximal and distal end portions of the lead, with suitable masking techniques being used to establish the respective lengths and shape configurations of the electrodes and the spaces therebetween. The deposited electrodes bond to the conductive links previously formed in the tunnels in the lead body so as to establish continuous electrical paths between the electrodes and their corresponding embedded conductors.

Finally, the connector contacts 44–50 are affixed to the connector body 42 at the proximal end of the lead, such contacts also being joined to the embedded spiral-wound conductors by the previously electroplated links and the deposited film electrodes. The proximal end of the lead supporting the contact rings 44–50 is then inserted into a mold and plastic is injection molded onto the lead to provide support for the contact rings.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and operating procedures, can be accomplished without departing from the scope of the invention itself.

The invention claimed is:

1. A neurostimulating lead comprising:
 a body member having a wall, a proximal end portion and a distal end portion;
 a first conductor within the wall of the body member and extending between the proximal end portion and the distal end portion;
 a second conductor within the wall of the body member and extending between the proximal end portion and the distal end portion, and wherein the first conductor and the second conductor are each spaced about the same distance from a longitudinal axis of the body member;
 a first opening in the wall in the distal end portion leading to the first conductor;
 a second opening in the wall in the distal end portion leading to the first conductor;
 a third opening in the wall in the distal end portion leading to the second conductor;
 a first conductive link within the first opening to electrically connect to the first conductor;
 a second conductive link within the second opening to electrically connect to the first conductor;
 a third conductive link within the third opening to electrically connect to the second conductor;
 a first band electrode positioned at the distal end portion and proximate the outer surface of the body member and electrically connected to the first conductive link and to the second conductive link; and
 a second band electrode positioned at the distal end portion proximate the outer surface of the body member and electrically connected to the third conductive link.

2. The neurostimulating lead in accordance with claim 1 further comprising at least one connector having a contact electrically joined to the first conductor at the proximal end portion of the body member and adapted to connect the lead to a neurostimulator.

3. The neurostimulating lead in accordance with claim 1 wherein the body member is tubular and having an annular wall defining an internal lumen extending between the proximal end portion and the distal end portion, and wherein the first conductor being spiral wound and embedded in the annular wall.

4. The neurostimulating lead in accordance with claim 3 wherein the body member comprises polyurethane and has an outer diameter of about 2 French and an internal diameter of about 0.012 inch.

5. The neurostimulating lead in accordance with claim 4 wherein the first conductor has a substantially rectangular cross-section about 0.004 inch wide by about 0.002 inch high.

6. The neurostimulating lead in accordance with claim 5 wherein the first conductor comprises metal, and wherein the metal is selected from a group consisting of stainless steel, MP35N, titanium, tantalum, tungsten, platinum, and silver.

7. The neurostimulating lead in accordance with claim 3 wherein the first conductor comprises turns, with each turn being at an angle between about 10 degrees to about 80 degrees from a longitudinal axis of the body member.

8. The neurostimulating lead in accordance with claim 7 wherein the electrode comprises a thin film electrode.

9. The neurostimulating lead in accordance with claim 1 wherein the first conductive link and the second conductive link comprise conductive epoxy.

10. The neurostimulating lead in accordance with claim 1 wherein the first conductive link and the second conductive link comprise an electroplated conductive link.

11. The neurostimulating lead in accordance with claim 10 wherein the electroplated conductive link comprises a metal selected from a group consisting of gold, silver, platinum, platinum-iridium and titanium.

12. The neurostimulating lead in accordance with claim 1 wherein the electrode comprises a thin film electrode, and the electrode comprises a first segment and a second segment disposed along a longitudinal dimension of the body member in overlapped relation, the first segment and the second segment adapted to be electrically connected to a one of a voltage of positive polarity, a voltage of negative polarity, and zero voltage.

13. The neurostimulating lead in accordance with claim 1 wherein the electrode comprises a thin film electrode, the thin film electrode comprising a first layer of a metal selected from a group consisting of titanium, chromium, nickel and aluminum and having a thickness less than about 5 microns and a second layer of a metal selected from the group consisting of gold, platinum, platinum-iridium, silver and copper and having a thickness between about 500 angstroms and about 50 microns.

14. The neurostimulating lead in accordance with claim 1 wherein the first conductor is embedded within the wall of the body member.

15. The medical lead in accordance with claim 1 further comprising a third conductor and a fourth conductor, and wherein the first conductor, the second conductor, the third conductor and the fourth conductor are each spaced about the same distance from a longitudinal axis of the body member.

16. A medical lead comprising:
a body member having a length, a surface, a proximal end portion and a distal end portion;
a first conductor extending substantially the length of the body member;
a first tunnel extending from the surface to the first conductor in the distal end portion;
a second tunnel extending from the surface to the first conductor in the distal end portion;
a first conductive link within the first tunnel and electrically connected to the first conductor;
a second conductive link within the second tunnel and electrically connected to the first conductor;
a first electrode positioned at the distal end portion of the body member, and wherein the first conductive link and the second conductive link are electrically connected to the first electrode;
a second conductor extending substantially the length of the body member, and wherein the first conductor and the second conductor are each spaced about the same distance from a longitudinal axis of the body member;
a third tunnel extending from the surface to the second conductor in the distal end portion;
a fourth tunnel extending from the surface to the second conductor in the distal end portion;
a third conductive link within the third tunnel and electrically connected to the second conductor;
a fourth conductive link within the fourth tunnel and electrically connected to the second conductor; and
a second electrode positioned at the distal end portion of the body member, and wherein the third conductive link and the fourth conductive link are electrically connected to second electrode.

17. A medical lead comprising:
a body member having a wall, a proximal end portion and a distal end portion;
a first conductor and a second conductor within the wall and extending substantially from the proximal end portion to the distal end portion, and wherein the first conductor and the second conductor are each spaced about the same distance from a longitudinal axis of the body member;
a first band electrode and a second band electrode positioned at a one of the proximal end portion and the distal end portion;
a first conductive link extending through the wall at the one of the proximal end portion and the distal end portion and electrically connecting the first conductor and the first electrode;
a second conductive link extending through the wall at the one of the proximal end portion and the distal end portion and electrically connecting the first conductor and the first electrode; and
a third conductive link extending through the wall at the one of the proximal end portion and the distal end portion and electrically connecting the second conductor and the second electrode.

18. The medical lead in accordance with claim 17 wherein the first conductive link comprises a conductive epoxy.

19. The medial lead in accordance with claim 17 wherein the first conductor is spirally wound, with each turn being at an angle between about 10 degrees to about 80 degrees from a longitudinal axis of the body member.

20. A medical lead, comprising:
a lead body having an insulator and having a first conductor and a second conductor spaced substantially equidistant from the axis of the lead body, and wherein the insulator comprises,
a first region formed by removal of at least a portion of the insulator in a distal end portion of the lead body, the first region exposing at least a portion of the first conductor,
a second region formed by removal of at least a portion of the insulator in the distal end portion of the lead body, the second region exposing at least a portion of the first conductor,
a third region formed by removal of at least a portion of the insulator in the distal end portion of the lead body, the third region exposing at least a portion of the second conductor,
a fourth region formed by removal of at least a portion of the insulator in the distal end portion of the lead body, the fourth region exposing at least a portion of the second conductor;
a first electrode electrically connected to the first conductor through the first region and electrically connected to the first conductor through the second region; and
a second electrode electrically connected to the second conductor through the third region and electrically connected to the second conductor through the fourth region.

21. The medical lead in accordance with claim 20 further comprising a third conductor and a fourth conductor, and wherein each of the first conductor, the second conductor, the third conductor and the fourth conductor are spaced substantially equidistant from the axis of the lead body.

22. The medical lead in accordance with claim 20 wherein the first conductor and the second conductor are spirally wound, with each turn being at an angle between about 10 degrees to about 80 degrees from a longitudinal axis of the lead.

23. A medical lead, comprising:
a lead body having an insulator and a first conductor and a second conductor, the first conductor and the second conductor spaced about the same distance from a longitudinal axis of the lead body, and wherein the insulator comprises,
  a first tunnel region formed by removal of at least a first portion of the insulator from the lead body, at least a portion of the first tunnel region formed to expose at least a first portion of the first conductor,
  a second tunnel region formed by removal of at least a second portion of the insulator from the lead body, at least a port on of the second tunnel region formed to expose at least a second portion of the first conductor,
  a third tunnel region formed by removal of at least a third portion of the insulator from the lead body, at least a portion of the third tunnel region formed to expose at least a first portion of the second conductor,
  a fourth tunnel region formed by removal of at least a fourth portion of the insulator from the lead body, at least a portion of the fourth tunnel region formed to expose at least a second portion of the second conductor, wherein the first, second, third and fourth tunnel regions are positioned on a distal end portion of the lead body;
a first conductive link having at least a portion thereof positioned within the first tunnel region, the first conductive link electrically connected to first conductor;
a second conductive link positioned within the second tunnel region, the second conductive link electrically connected to the first conductor;
a third conductive link having at least a portion thereof positioned within the third tunnel region, the third conductive link electrically connected to second conductor;
a fourth conductive link positioned within the second tunnel region, the fourth conductive link electrically connected to the second conductor;
a first band electrically connected to the first conductive link and electrically connected to the second conductive link; and
a second band electrically connected to the third conductive link and electrically connected to the fourth conductive link.

24. The medical lead in accordance with claim 23 wherein each of the tunnel regions comprise a channel cut in the insulator.

25. The medical lead in accordance with claim 23 wherein the first conductive link comprises electroplating material.

26. The medical lead in accordance with claim 23 wherein the first conductive link comprises a conductive epoxy.

27. A medical lead, comprising:
a lead body having an insulator, a first conductor and a second conductor each spaced about the same distance from a longitudinal axis of the body member, wherein the insulator comprises,
  a first opening formed by removal of at least a first portion of the insulator from a distal end portion of the lead body, at least a portion of the first opening formed to expose at least a first portion of the first conductor,
  a second opening formed by removal of at least a second portion of the insulator from a distal end portion of the lead body, at least a portion of the second opening formed to expose at least a second portion of the first conductor,
  a third opening formed by removal of at least a third portion of the insulator from a distal end portion of the lead body, at least a portion of the third opening formed to expose at least a first portion of the second conductor, and
  a fourth opening formed by removal of at least a fourth portion of the insulator from a distal end portion of the lead body, at least a portion of the fourth opening formed to expose at least a second portion of the second conductor;
a first conductive link within the first opening, the first conductive link electrically connected to the first conductor;
a second conductive link within the second opening, the second conductive link electrically connected to the first conductor;
a third conductive link within the third opening, the third conductive link electrically connected to the second conductor;
a fourth conductive link within the fourth opening, the fourth conductive link electrically connected to the second conductor;
a first band electrode electrically connected to the first conductive link to electrically connect the first band to the first conductor, and electrically connected to the second conductive link to electrically connect the first band to the first conductor; and
a second band electrode electrically connected to the third conductive link to electrically connect the second band to the second conductor, and electrically connected to the fourth conductive link to electrically connect the second band to the second conductor.

28. The medical lead in accordance with claim 27 wherein the first conductor and the second conductor extend substantially the length of the lead body and are spirally wound about a longitudinal axis of the lead body.

29. The medical lead in accordance with claim 28 wherein the first conductive link and the second conductive link comprise a one of an electroplating material and a conductive epoxy.

* * * * *